US006824570B2

(12) United States Patent
Vidal et al.

(10) Patent No.: US 6,824,570 B2
(45) Date of Patent: Nov. 30, 2004

(54) COMPOSITION FOR DYEING HUMAN KERATIN FIBRES, COMPRISING A PARTICULAR MONOCATIONIC MONOAZO DYE

(75) Inventors: Laurent Vidal, Paris (FR); Aziz Fadli, Chelles (FR)

(73) Assignee: L'Oreal S.A. (FR)

( * ) Notice: Subject to any disclaimer, the term of this patent is extended or adjusted under 35 U.S.C. 154(b) by 239 days.

(21) Appl. No.: 10/254,798

(22) Filed: Sep. 26, 2002

(65) Prior Publication Data

US 2003/0106169 A1 Jun. 12, 2003

(30) Foreign Application Priority Data

Sep. 26, 2001 (FR) .............................. 01 12374

(51) Int. Cl.$^7$ ................................. A61K 7/13
(52) U.S. Cl. ................. 8/405; 8/406; 8/407; 8/437; 8/441; 8/451; 8/463; 8/568; 8/570; 8/572; 8/573; 8/574; 132/202; 132/208
(58) Field of Search ............................ 8/405, 407, 437, 8/441, 451, 463, 568, 570, 572, 573, 574; 132/202, 208

(56) References Cited

U.S. PATENT DOCUMENTS

| | | | |
|---|---|---|---|
| 3,585,182 A | 6/1971 | Stanley et al. ............... 260/157 |
| 3,741,982 A | * 6/1973 | Fujino et al. ................ 548/402 |
| 4,003,699 A | 1/1977 | Rose et al. .................... 8/10.2 |
| 4,823,985 A | 4/1989 | Grollier et al. ................ 222/1 |
| 5,061,289 A | 10/1991 | Clausen et al. ................ 8/405 |
| 5,208,325 A | 5/1993 | Berneth et al. .............. 534/607 |
| 5,380,340 A | 1/1995 | Neunhoeffer et al. .......... 8/409 |
| 5,436,323 A | 7/1995 | Berneth et al. .............. 534/607 |
| 5,708,151 A | 1/1998 | Möckli ........................ 534/608 |
| 5,766,576 A | 6/1998 | Löwe et al. ................... 426/62 |
| 6,001,135 A | 12/1999 | Rondeau et al. ................ 8/407 |
| 6,099,592 A | 8/2000 | Vidal et al. ..................... 8/409 |
| 6,368,360 B2 | 4/2002 | Samain ........................... 8/426 |

FOREIGN PATENT DOCUMENTS

| | | |
|---|---|---|
| DE | 23 59 399 | 6/1975 |
| DE | 38 43 892 | 6/1990 |
| DE | 41 33 957 | 4/1993 |
| DE | 195 43 988 | 5/1997 |
| EP | 0 714 954 | 6/1996 |
| EP | 0 770 375 | 5/1997 |
| EP | 0 846 948 | 6/1998 |
| FR | 1 584 965 | 1/1970 |
| FR | 2 586 913 | 5/1987 |
| FR | 2 733 749 | 11/1996 |
| FR | 2 741 798 | 6/1997 |
| GB | 1 153 196 | 5/1969 |
| GB | 1 276 686 | 6/1972 |
| GB | 1 360 562 | 7/1974 |
| GB | 1 026 978 | 4/1996 |
| JP | 55-22638 | 2/1980 |
| JP | 2-19576 | 1/1990 |
| JP | 5-163124 | 6/1993 |
| WO | WO 94/08969 | 4/1994 |
| WO | WO 94/08970 | 4/1994 |
| WO | WO 95/01772 | 1/1995 |
| WO | WO 95/15144 | 6/1995 |
| WO | WO 96/16765 | 5/1996 |

OTHER PUBLICATIONS

Database CA, Chemical Abstracts Service, Columbus, Ohio, US; Chernov'yants, M. S. et al: "Quaternary 2–azobenzimidazolium salts as indicators with overlapping protonation regions," Database Accession No. 127:67344 XP002199537, 1997.

Database CA, Chemical Abstracts Service, Columbus, Ohio, US; Evlashenkova, I.V. et al: "Acidity function H+ of sulfuric acid solutions," Database Accession No. 126:217134 XP002199538, 1996.

Database CA, Chemical Abstracts Service, Columbus, Ohio, US; Sogomonova, R.A. et al: "Amination of areneazobenzimidazolium salts," Database Accession No. 94:103240 XP002199550, 1980.

English language Derwent Abstract of EP 0 770 375, May 2, 1977.

English language Derwent Abstract of FR 1 584 965, Jan. 9, 1970.

English language Derwent Abstract of JP 55–22638, Feb. 18, 1980.

English language Derwent Abstract of JP 2–19576, Jan. 23, 1990.

English language Derwent Abstract of JP 5–153124, Jun. 29, 1993.

* cited by examiner

*Primary Examiner*—Mark Kopec
*Assistant Examiner*—Eisa Elhilo
(74) *Attorney, Agent, or Firm*—Finnegan, Henderson, Farabow, Garrett & Dunner, L.L.P.

(57) ABSTRACT

A dye composition for dyeing human keratin fibers, such as hair, comprising at least one monocationic monoazo dye of formula (I)

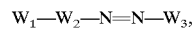

$$W_1-W_2-N=N-W_3,$$

a dyeing process using the composition and certain novel compounds of formula (I).

56 Claims, No Drawings

COMPOSITION FOR DYEING HUMAN KERATIN FIBRES, COMPRISING A PARTICULAR MONOCATIONIC MONOAZO DYE

The present invention relates to a dye composition for dyeing human keratin fibres, such as hair, comprising at least one monocationic monoazo dye. The present invention also relates to the processes for dyeing human keratin fibres, such as hair, using such a composition. The present invention further relates to novel monocationic monoazo compounds.

It is a known practice to dye human keratin fibres, such as hair, with dye compositions containing oxidation dye precursors, generally referred to as oxidation bases, such as ortho- or para-phenylenediamines, ortho- or para-aminophenols, and heterocyclic compounds. These oxidation bases are generally colourless or weakly coloured compounds that, when combined with oxidizing agents, may give rise to coloured compounds by a process of oxidative condensation.

It is also known that the shades obtained with these oxidation bases can be varied by combining them with couplers or colour modifiers. These couplers or colour modifiers may be chosen, for example, from aromatic meta-diamines, meta-aminophenols, meta-diphenols, and certain heterocyclic compounds such as indole compounds.

The variety of molecules used as oxidation bases and couplers can allow for a wide range of colours to be obtained.

This oxidation dyeing process comprises applying to the keratin fibres, oxidation bases or a mixture of oxidation bases and couplers, with an oxidizing agent, for example, aqueous hydrogen peroxide; leaving the mixture to stand on the fibres; and then rinsing the fibres. The colorations which result from the oxidation dyeing process can be permanent, strong, and resistant to external agents, such as light, bad weather, washing, perspiration, and rubbing. The oxidation dyeing process, which is generally applied at basic pH, makes it possible to obtain dyeing and simultaneously lightening of the fibre, making it possible to obtain a final coloration that is lighter than the original colour. Additionally, the lightening of the fibre can have the advantageous effect of giving rise to a uniform colour in the case of grey hair, and, in the case of naturally pigmented hair, of bringing the colour out, i.e., of making it more visible.

It is also a known practice to dye human keratin fibres by direct dyeing. The process conventionally used in direct dyeing comprises applying to the keratin fibres direct dyes, which are coloured, and colouring molecules having an affinity for the fibres, leaving the dyes to stand on the fibres, and then rinsing the fibres.

It is also a known practice, for example, to use nitrobenzene, anthraquinone or nitropyridine direct dyes, azo, xanthene, acridine or azine dyes or triarylmethane dyes.

The resulting colorations from the direct dyes can be chromatic colorations that can, however, be temporary or semi-permanent. The nature of the interactions that bind the direct dyes to the keratin fibre, and their desorption from the surface and/or from the core of the fibre, can be responsible for their weak dyeing capacity, and for their poor resistance to washing or to perspiration. These direct dyes can also be sensitive to light due to the poor resistance of the chromophore to photochemical attacks that lead, over time, to a dulling of the coloration of the hair. Additionally, their sensitivity to light is dependent on whether they are distributed uniformly or in aggregates in the keratin fibre.

Another known practice is to use direct dyes in combination with oxidizing agents. However, the direct dyes can be sensitive to the action of oxidizing agents such as aqueous hydrogen peroxide, and reducing agents such as sodium bisulphite, which generally makes them difficult to use in lightening direct dye compositions based on aqueous hydrogen peroxide and on a basifying agent, or in oxidation dyeing compositions in combination with precursors such as oxidation bases or couplers.

For example, in patent applications FR-1 584 965 and JP-062 711 435, it has been proposed to dye the hair with dye compositions based on direct nitro dyes, and/or on dispersed azo dyes, and on ammoniacal aqueous hydrogen peroxide, by applying to the hair a mixture of said dyes and of said oxidant, prepared just before use. The colorations obtained by this approach, however, can prove to be insufficiently durable, and disappear with shampooing, thus allowing lightening of the hair fibre to appear. By changing over time, such a coloration becomes unaesthetic.

In patent applications JP-53 95693 and JP-55 022638, it has also been proposed to dye the hair with compositions based on cationic direct dyes of the oxazine type and of ammoniacal aqueous hydrogen peroxide, by applying to the hair, in a first step, ammoniacal aqueous hydrogen peroxide, and in a second step, a composition based on the oxazine direct dye. This coloration can be unsatisfactory, due to the fact that it requires a process in which the product needs to be left to stand on the hair for a long time in the two successive steps. If, moreover, an extemporaneous mixture of the oxazine direct dye with ammoniacal aqueous hydrogen peroxide is applied to the hair, then no coloration can be obtained or, at the very least, a virtually nonexistent coloration of the hair fibre can be obtained.

More recently, patent application FR 2 741 798 described dye compositions containing direct dyes comprising at least one quarternized nitrogen atom of the azo or azomethine type, wherein said compositions need to be mixed extemporaneously at basic pH with an oxidizing composition. These compositions make it possible to obtain colorations with homogeneous, durable, and brilliant glints. However, they may not dye keratin fibres with as much strength as oxidation dyeing compositions.

There is therefore a need for chromatic direct dyes which can dye human keratin fibres as strongly as oxidation dyes, and/or can be as stable as oxidation dyes when exposed to light, bad weather, washing, and perspiration. Additionally, there is a need for chromatic direct dyes that can be sufficiently stable in the presence of oxidizing and reducing agents to be able to obtain simultaneously a lightening of the fibre either by using direct lightening compositions comprising them, or by using oxidation dye compositions based on oxidation dye precursors comprising them. There is also a need for direct dyes which can dye human keratin fibres in a wide range of colours, such as chromatic colours, as well as the "fundamental" shades such as blacks and browns.

The present invention therefore relates to a composition for dyeing human keratin fibres, such as hair, comprising, in a cosmetically acceptable medium, at least one monocationic monoazo dye of formula (I) below:

$$W_1-W_2-N=N-W_3 \qquad \text{Formula (I)}$$

wherein:

$W_1$ is chosen from 5-, 6-, 7- and 8-membered heterocycles of formula (II) below:

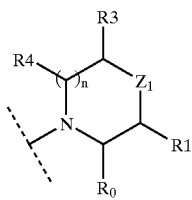

Formula (II)

$W_2$ is chosen from divalent, aromatic, and carbon-based pyridines and pyridazines of formula (III) below:

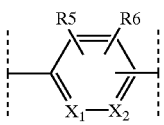

Formula (III)

$W_3$ is chosen from cationic heteroaromatic radicals of formula (IV) below:

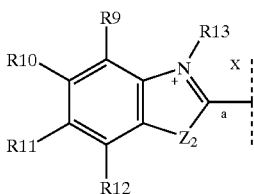

(IV)

wherein in formulae (II), (III) and (IV):

n=0, 1, 2 or 3, provided that when n is greater than or equal to 2, then the $R_4$ radicals may be identical or different, $X_1$ is chosen from a nitrogen atom and $CR_7$ radicals, $X_2$ is chosen from a nitrogen atom and $CR_8$ radicals, $Z_1$ is chosen from $CHR_2$ radicals, oxygen and sulphur atoms, and $NR_{14}$ radicals, $Z_2$ is chosen from oxygen and sulphur atoms, and $NR_{15}$ radicals, $R_0$, $R_1$, $R_2$, $R_3$, $R_4$, $R_5$, $R_6$, $R_7$, $R_8$, $R_9$, $R_{10}$, $R_{11}$ and $R_{12}$, which may be identical or different, are each chosen from a hydrogen atom, linear and branched $C_1$–$C_{10}$ hydrocarbon-based chains, possibly forming at least one carbon-based ring comprising from 3 to 6 members, and being saturated or unsaturated, wherein at least one carbon atom of the hydrocarbon-based chains may be replaced with an entity chosen from oxygen, nitrogen, and sulphur atoms, and an $SO_2$ group, and wherein the carbon atoms may be, independently of one another, substituted, for example, with at least one halogen atom; $R_0$, $R_1$, $R_2$, $R_3$, $R_4$, $R_5$, $R_6$, $R_7$, $R_8$, $R_9$, $R_{11}$ and $R_{12}$ comprising no peroxide bond, nor any diazo or nitroso radicals, $R_{14}$ is chosen from a hydrogen atom, linear and branched $C_1$–$C_{10}$ hydrocarbon-based chains, possibly forming at least one carbon-based ring comprising from 3 to 6 members, and being saturated or unsaturated, wherein at least one carbon atom of the hydrocarbon-based chains may be replaced with an entity chosen from oxygen, nitrogen and sulphur atoms, and an $SO_2$ group, and wherein the carbon atoms may be, independently of one another, substituted, for example, with at least one halogen atom, $R_{14}$ comprising no peroxide bond, nor any diazo or nitroso radicals; provided that said oxygen, nitrogen and sulphur atoms are not linked directly to the nitrogen atom carrying the $R_{14}$ radical, $R_5$ with $R_6$ may optionally form a carbon-based aromatic ring, such as phenyl, $R_{13}$ and $R_{15}$, which may be identical or different, are each chosen from $C_1$–$C_8$ alkyl radicals optionally substituted with at least one radical chosen from hydroxyl, $C_1$–$C_2$ alkoxy, and $C_2$–$C_4$ (poly)hydroxyalkoxy, unsubstituted and substituted amino, such as unsubstituted amino and $C_1$–$C_2$ (di)alkylamino, carboxyl, sulphonic, and phenyl radicals which are optionally substituted;

the bond a of the cationic ring of formula (IV) is linked to the azo group of formula (I);

X is an anion chosen from organic and inorganic anions.

According to the invention, when it is indicated that at least one of the carbon atoms of the hydrocarbon-based chains defined for $R_0$, $R_1$, $R_2$, $R_3$, $R_4$, $R_5$, $R_6$, $R_7$, $R_8$, $R_9$, $R_{10}$, $R_{11}$, $R_{12}$ and $R_{14}$ may be replaced with an entity chosen from oxygen, nitrogen, and sulphur atoms, and an $SO_2$ group, and/or that the hydrocarbon-based chains are unsaturated, this means that it is possible, by way of example, to make the following transformation:

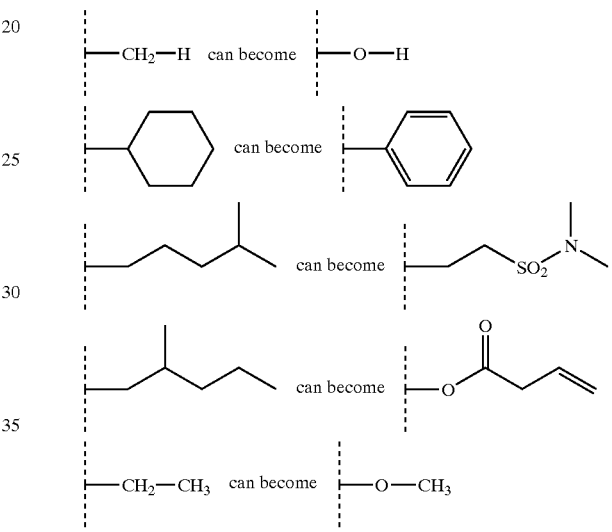

As used herein, the expression "branched hydrocarbon-based chain" means a chain which can form at least one carbon-based ring comprising from 3 to 6 members. The expression "unsaturated hydrocarbon-based chain" means a chain which can comprise at least one double bond and/or at least one triple bond, said hydrocarbon-based chain optionally being able to form aromatic groups.

X is an anion chosen from organic and inorganic anions, for example, halides, such as chloride, bromide, fluoride and iodide; hydroxides; sulphates; hydrogen sulphates; $(C_1$–$C_6)$ alkyl sulphates, such as methyl sulphate and ethyl sulphate; acetates; tartrates; oxalates; $(C_1$–$C_6)$ alkylsulphonates, such as methylsulphonate; and arylsulphonates which may be substituted with at least one radical chosen from $C_1$–$C_4$ alkyl radicals, such as 4-tolylsulphonate.

In a further embodiment of the present invention, $R_1$, $R_2$, and $R_3$, which may be identical or different, are each chosen from a hydrogen atom; alkoxy, hydroxyl, unsubstituted amino, and acetoxy radicals; linear and branched $C_1$–$C_4$ alkyl radicals substituted with at least one substituent chosen from halogen atoms, hydroxyl, $C_1$–$C_2$ alkoxy, (poly)hydroxyalkoxy, unsubstituted amino, $C_1$–$C_2$ (di)alkylamino, carboxyl and sulphonic radicals; and —$NR_{16}R_{17}$ groups, wherein $R_{16}$ and $R_{17}$, which may be identical or different, are each chosen from a hydrogen atom, methylsulphonyl, carboxyl, carboxamido, and $C_1$–$C_4$ alkyl radicals substituted with at least one substituent chosen from halogen atoms, hydroxyl, $C_1$–$C_2$ alkoxy, unsubstituted amino, $C_1$–$C_2$ (di) alkylamino, and carboxyl radicals.

The asymmetric carbons of said 5-, 6-, 7- and 8-membered heterocycles of formula (II) may, independently of one another, have the configuration (R) or (S).

In another embodiment of the present invention, $R_1$, $R_2$, and $R_3$, which may be identical or different, are each chosen from a hydrogen atom; a hydroxyl radical; and amino radicals which are optionally mono- or disubstituted; and linear and branched $C_1$–$C_3$ alkyl radicals optionally substituted with at least one radical chosen from hydroxyl, $C_1$–$C_2$ alkoxy, unsubstituted amino, $C_1$–$C_2$ (di)alkylamino, carboxyl, and sulphonic radicals.

In another embodiment of the present invention, $R_1$, $R_2$, and $R_3$, which may be identical or different, are each chosen from a hydrogen atom; methyl radicals, such as methyl and hydroxymethyl; a hydroxyl radical; and unsubstituted and substituted amino radicals, such as unsubstituted amino, (di)methylamino, methylsulphonylamino, and $C_2$–$C_4$ (poly) hydroxyalkylamino.

According to one embodiment of the invention in formula (II), $R_1$ is chosen, for example, from a hydrogen atom, and methyl, hydroxyl, and unsubstituted and substituted amino, such as unsubstituted amino, methylamino, dimethylamino, and 2-hydroxyethylamino radicals, and further for example, from a hydrogen atom, a hydroxyl radical, an, unsubstituted amino radical, and a dimethylamino radical, and even further for example from a hydrogen atom and a hydroxyl radical.

According to one embodiment of the present invention, in formula (II), $R_0$ is chosen from, for example, a hydrogen atom, and linear and branched $C_1$–$C_4$ alkyl radicals substituted with at least one radical chosen from hydroxyl, methoxy, unsubstituted amino, (di)alkylamino, carboxyl, sulphonyl, amido, and dimethylamido radicals, even further for example, $R_0$ may be chosen from a hydrogen atom, and carboxyl, amido, dimethylamido, and hydroxymethyl radicals. In another further example, $R_0$ is a hydrogen atom.

In one example of the present invention, $Z_1$ is chosen from $NR_{14}$ and $CHR_2$ radicals. Further, for example, $Z_1$ is chosen from $CHR_2$ radicals.

In another embodiment, $Z_1$ in formula (II) is chosen from $CH_2$, CHOH, $CHNH_2$, and $CHN(CH_3)_2$, and in a further embodiment, $Z_1$ in formula (II) is $CH_2$.

According to another embodiment, n in formula (II) is 0 or 1. In a further embodiment, n is 0.

The radicals $R_5$, $R_6$, $R_7$, $R_8$, $R_9$, $R_{10}$, $R_{11}$ and $R_{12}$, which may be identical or different, are, for example, each chosen from a hydrogen atom, and methyl, ethyl, isopropyl, methoxymethyl, hydroxymethyl, 1-carboxymethyl, 1-aminomethyl, 2-carboxyethyl, 2-hydroxyethyl, 3-hydroxypropyl, 1,2-dihydroxyethyl, 1-hydroxy-2-aminoethyl, 2-hydroxy-1-aminoethyl, methoxy, ethoxy, 2-hydroxyethyloxy, 3-aminoethyloxy, unsubstituted amino, methylamino, dimethylamino, and 2-hydroxyethylamino radicals.

In another embodiment, $R_5$, $R_6$, $R_7$, $R_8$, $R_9$, $R_{10}$, $R_{11}$ and $R_{12}$, which may be identical or different, are each chosen from, for example, a hydrogen atom, and methyl, hydroxymethyl, 2-hydroxyethyl, 1,2-dihydroxyethyl, methoxy, 2-hydroxyethyloxy, unsubstituted amino, and 2-hydroxyethylamino radicals, and in a further embodiment, $R_5$, $R_6$, $R_7$, $R_8$, $R_9$, $R_{10}$, $R_{11}$ and $R_{12}$, which may be identical or different, are each chosen from a hydrogen atom, and methyl, methoxy, and unsubstituted amino radicals.

According to another embodiment of the invention, $X_1$ of formula (III) may be chosen from $CR_7$ radicals, wherein $R_7$ is defined as above, and $X_2$ of formula (III) may be chosen from $CR_8$ radicals, wherein $R_8$ is defined as above.

According to another embodiment of the invention, $R_{13}$ and $R_{15}$, which may be identical or different, are each chosen from $C_1$–$C_4$ alkyl radicals optionally substituted with at least one radical chosen from hydroxyl, $C_1$–$C_2$ alkoxy, unsubstituted amino, $C_1$–$C_2$ (di)alkylamino, carboxyl, sulphonic, and phenyl radicals, and for example, methyl, ethyl, 2-hydroxyethyl, 1-carboxymethyl, 2-carboxyethyl, and 2-sulphonylethyl radicals.

In one embodiment, $R_{13}$ and $R_{15}$, which may be identical or different, are each chosen from $C_1$–$C_3$ alkyls optionally substituted with at least one radical chosen from hydroxyl, methoxy, unsubstituted amino, dimethylamino, carboxyl, and sulphonic radicals.

In another embodiment, $R_{13}$ and $R_{15}$, which may be identical or different, are each chosen from, for example, methyl, ethyl, 2-hydroxyethyl, and carboxymethyl radicals, and further for example, from a methyl radical.

According to an embodiment of the invention, $R_{14}$ is chosen from a hydrogen atom, and linear and branched $C_1$–$C_3$ alkyl radicals optionally substituted with at least one radical chosen from hydroxy, methoxy, unsubstituted amino, methylamino, dimethylamino, carboxyl, and sulphonyl radicals.

According to another embodiment, $R_{14}$ is chosen from a hydrogen atom, and methyl and 2-hydroxyethyl radicals.

According to another embodiment, $Z_2$ is chosen from $NR_{15}$ with all the above mentioned designations provided for $R_{15}$.

According to another embodiment, $R_0$, $R_1$, $Z_1$, $R_3$, $R_4$ and n are each chosen from the following combinations:

| $R_0$ | $R_1$ | $Z_1$ | $R_3$ | $R_4$ | n |
|---|---|---|---|---|---|
| H | H | $CH_2$ | H | H | 0, 1, 2, 3 |
| H | H | N $CH_3$ | H | H | 0 or 1 |
| H | H | N—$CH_2$—$CH_2$—OH | H | H | 0 or 1 |
| $CH_3$ | $CH_3$ | $CH_2$ | H | H | 0 or 1 |
| COOH | H | $CH_2$ | H | H | 0, 1, 2 |
| COOH | OH | $CH_2$ | H | H | 0 or 1 |
| COOH | H | CH—OH | H | H | 0 |
| COOH | H | CH—COOH | H | H | 0 |
| $CH_2$—OH | OH | CH—OH | H | H | 0 |
| $CH_2$—O $CH_3$ | H | $CH_2$ | $CH_2$—O $CH_3$ | H | 0 |
| $CONH_2$ | H | $CH_2$ | H | H | 0, 1, 2 |
| $CONH_2$ | OH | $CH_2$ | H | H | 0 or 1 |
| $CON(CH_3)_2$ | H | $CH_2$ | H | H | 0, 1, 2 |

-continued

| $R_0$ | $R_1$ | $Z_1$ | $R_3$ | $R_4$ | n |
|---|---|---|---|---|---|
| $CON(CH_3)_2$ | OH | $CH_2$ | H | H | 0 or 1 |
| $CH_2OH$ | H | $CH_2$ | H | H | 0 or 1 |
| $CH_2OH$ | OH | $CH_2$ | H | H | 0 or 1 |
| $CH_2OH$ | H | $CH_2$ | $CH_2OH$ | H | 0 |
| H | OH | $CH_2$ | H | H | 0 or 1 |
| H | OH | CH—OH | H | H | 0 or 1 |
| H | $NH_2$ | $CH_2$ | H | H | 0 or 1 |
| H | $NH\,CH_3$ | $CH_2$ | H | H | 0 or 1 |
| H | $N(CH_3)_2$ | $CH_2$ | H | H | 0 or 1 |
| H | OH | CH—$NH_2$ | H | H | 0 or 1 |
| H | OH | CH—NH $CH_3$ | H | H | 0 or 1 |
| H | OH | CH—NH—$CH_2$—CH—OH | H | H | 0 or 1 |
| H | OH | CH—OH | OH | OH | 2 |
| $CH_3$ | H | $CH_2$ | H | H | 1 |
| H | H | CH—OH | H | H | 1 |
| $CH_3$ | H | $CH_2$ | H | $CH_3$ | 1 |
| $CH_2$—$NH_2$ | H | $CH_2$ | H | $CH_3$ | 1 |
| $CH_3$ | H | CH—$NH_2$ | H | H | 1 |
| H | $CH_2$—OH | $CH_2$ | H | H | 1 |
| H | H | CH—CH—OH | H | H | 1 |
| H | CO—$NH_2$ | $CH_2$ | H | H | 1 |
| H | COOH | $CH_2$ | H | H | 1 |
| H | H | $CH_2$—COOH | H | H | 1 |
| H | H | $CH_2$ | H | H | 1 |
| H | H | CH-$N(CH_3)_2$ | H | H | 1 |

In a further embodiment, $R_0$, $R_1$, $Z_1$, $R_3$, $R_4$ and n are each chosen from the following combinations:

| $R_0$ | $R_1$ | $Z_1$ | $R_3$ | $R_4$ | n |
|---|---|---|---|---|---|
| COOH | H | $CH_2$ | H | H | 0 |
| COOH | OH | $CH_2$ | H | H | 0 |
| $CON(CH_3)_2$ | H | $CH_2$ | H | H | 0 |
| $CONH_2$ | H | $CH_2$ | H | H | 0 |
| $CH_2OH$ | H | $CH_2$ | H | H | 0 |
| $CH_2OH$ | OH | $CH_2$ | H | H | 0 |
| H | OH | $CH_2$ | H | H | 0 |
| H | $NH_2$ | $CH_2$ | H | H | 0 |
| H | $NH(CH_3)_2$ | $CH_2$ | H | H | 0 |

The at least one monocationic monoazo dye of formula (I), may be chosen from, for example:

1,3-dimethyl-2-[4-(pyrrolidin-1-yl)phenylazo] benzimidazol-1-ium,
1,3-dimethyl-2-[4-(3-hydroxypyrrolidin-1-yl)phenylazo] benzimidazol-1-ium,
1,3-dimethyl-2-[4-(2-carboxypyrrolidin-1-yl)phenylazo] benzimidazol-1-ium,
1,3-dimethyl-2-[4-(3-aminopyrrolidin-1-yl)phenylazo] benzimidazol-1-ium,
1,3-dimethyl-2-[4-(2-carboxy-3-hydroxypyrrolidin-1-yl) phenylazo]benzimidazol-1-ium,
1,3-dimethyl-2-[4-(2-carboxamidopyrrolidin-1-yl) phenylazo]benzimidazol-1-ium,
1,3-dimethyl-2-[4-(2-hydroxymethylpyrrolidin-1-yl) phenylazo]benzimidazol-1-ium,
1,3-dimethyl-2-[4-(2-carboxy-4-hydroxypyrrolidin-1-yl) phenylazo]benzimidazol-1-ium,
1,3-dimethyl-2-[4-(piperidin-1-yl)phenylazo]benzimidazol-1-ium,
1,3-dimethyl-2-[4-(3-hydroxypiperidin-1-yl)phenylazo] benzimidazol-1-ium,
1,3-dimethyl-2-[4-(3-hydroxymethylpiperidin-1-yl) phenylazo]benzimidazol-1-ium,
1,3-dimethyl-2-[4-(3-carboxypiperidin-1-yl)phenylazo] benzimidazol-1-ium,
1,3-dimethyl-2-[4-(2-carboxypiperidin-1-yl)phenylazo] benzimidazol-1-ium,
1,3-dimethyl-2-[4-(piperazin-1-yl)phenylazo]benzimidazol-1-ium,
1,3-dimethyl-2-[4-(homopiperazin-1-yl)phenylazo] benzimidazol-1-ium,
5-amino-1,3-dimethyl-2-[4-(pyrrolidin-1-yl)phenylazo] benzimidazol-1-ium,
5-amino-1,3-dimethyl-2-[4-(3-hydroxypyrrolidin-1-yl) phenylazo]benzimidazol-1-ium,
5-amino-1,3-dimethyl-2-[4-(2-carboxypyrrolidin-1-yl) phenylazo]benzimidazol-1-ium,
5-amino-1,3--dimethyl-2-[4-(3-aminopyrrolidin-1-yl) phenylazo]benzimidazol-1-ium,
5-amino-1,3-dimethyl-2-[4-(2-carboxy-3-hydroxy-pyrrolidin-1-yl)phenylazo]benzimidazol-1-ium,
5-amino-1,3-dimethyl-2-[4-(2-carboxamidopyrrolidin-1-yl) phenylazo]benzimidazol-1-ium,
5-amino-1,3-dimethyl-2-[4-(2-hydroxymethylpyrrolidin-1-yl)phenylazo]benzimidazol-1-ium,
5-amino-1,3-dimethyl-2-[4-(2-carboxy-4-hydroxy-pyrrolidin-1-yl)phenylazo]benzimidazol-1-ium,
5-amino-1,3-dimethyl-2-[4-(piperidin-1-yl)phenylazo] benzimidazol-1-ium,
5-amino-1,3-dimethyl-2-[4-(3-hydroxypiperidin-1-yl) phenylazo]benzimidazol-1-ium,
5-amino-1,3-dimethyl-2-[4-(3-hydroxymethylpiperidin-1-yl)phenylazo]benzimidazol-1-ium,
5-amino-1,3-dimethyl-2-[4-(3-carboxypiperidin-1-yl) phenylazo]benzimidazol-1-ium,
5-amino-1,3-dimethyl-2-[4-(2-carboxypiperidin-1-yl) phenylazo]benzimidazol-1-ium,
5-amino-1,3-dimethyl-2-[4-(piperazin-1-yl)phenylazo] benzimidazol-1-ium,
5-amino-1,3-dimethyl-2-[4-(homopiperazin-1-yl) phenylazo]benzimidazol-1-ium,
5-dimethylamino-1,3-dimethyl-2-[4-(pyrrolidin-1-yl) phenylazo]benzimidazol-1-ium,
5-dimethylamino-1,3-dimethyl-2-[4-(3-hydroxypyrrolidin-1-yl)phenylazo]benzimidazol-1-ium,
5-dimethylamino-1,3-dimethyl-2-[4-(2-carboxypyrrolidin-1-yl)phenylazo]benzimidazol-1-ium, 5-dimethylamino-1,3-dimethyl-2-[4-(3-aminopyrrolidin-1-yl)phenylazo]benzimidazol-1-ium,
5-dimethylamino-1,3-dimethyl-2-[4-(2-carboxy-3-hydroxypyrrolidin-1-yl)phenylazo]benzimidazol-1-ium,
5-dimethylamino-1,3-dimethyl-2-[4-(2-carboxamido-pyrrolidin-1-yl)phenylazo]benzimidazol-1-ium,
5-dimethylamino-1,3-dimethyl-2-[4-(2-hydroxymethyl-pyrrolidin-1-yl)phenylazo]benzimidazol-1-ium,
5-dimethylamino-1,3-dimethyl-2-[4-(2-carboxy-4-hydroxypyrrolidin-1-yl)phenylazo]benzimidazol-1-ium,
5-dimethylamino-1,3-dimethyl-2-[4-(piperidin-1-yl)phenylazo]benzimidazol-1-ium,
5-dimethylamino-1,3-dimethyl-2-[4-(3-hydroxypiperidin-1-yl)phenylazo]benzimidazol-1-ium,
5-dimethylamino-1,3-dimethyl-2-[4-(3-hydroxymethyl-piperidin-1-yl)phenylazo]benzimidazol-1-ium,
5-dimethylamino-1,3-dimethyl-2-[4-(3-carboxypiperidin-1-yl)phenylazo]benzimidazol-1-ium,
5-dimethylamino-1,3-dimethyl-2-[4-(2-carboxypiperidin-1-yl)phenylazo]benzimidazol-1-ium,
5-dimethylamino-1,3-dimethyl-2-[4-(piperazin-1-yl)phenylazo]benzimidazol-1-ium, and
5-dimethylamino-1,3-dimethyl-2-[4-(homopiperazin-1-yl)phenylazo]benzimidazol-1-ium.

The concentration of said at least one monocationic monoazo dye of formula (I) may range, for example, from about 0.001% to about 5% by weight relative to the total weight of the dye composition, and for example, from about 0.05% to about 2% by weight relative to the total weight of the dye composition.

The dye composition in accordance with the invention may further comprise at least one additional direct dye which is different from those of formula (I). For example, the at least one additional direct dye may be chosen from neutral, acidic, and cationic nitrobenzene direct dyes; neutral, acidic and cationic azo direct dyes; neutral, acidic and cationic quinone direct dyes, such as anthraquinone direct dyes; azine direct dyes; methine direct dyes; triarylmethane direct dyes; indoamine direct dyes; and natural direct dyes.

Among nitrobenzene direct dyes, mention may be made, for example, of the following compounds:

1,4-diamino-2-nitrobenzene
1-amino-2-nitro-4-β-hydroxyethylaminobenzene
1-amino-2-nitro-4-bis(β-hydroxyethyl)aminobenzene
1,4-bis(β-hydroxyethylamino)-2-nitrobenzene
1-β-hydroxyethylamino-2-nitro-4-bis(β-hydroxyethyl-amino)benzene
1-β-hydroxyethylamino-2-nitro-4-aminobenzene
1-β-hydroxyethylamino-2-nitro-4-(ethyl)(β-hydroxyethyl)aminobenzene
1-amino-3-methyl-4-β-hydroxyethylamino-6-nitrobenzene
1-amino-2-nitro-4-β-hydroxyethylamino-5-chlorobenzene
1,2-diamino-4-nitrobenzene
1-amino-2-β-hydroxyethylamino-5-nitrobenzene
1,2-bis(β-hydroxyethylamino)-4-nitrobenzene
1-amino-2-tris(hydroxymethyl)methylamino-5-nitrobenzene
1-hydroxy-2-amino-5-nitrobenzene
1-hydroxy-2-amino-4-nitrobenzene
1-hydroxy-3-nitro-4-aminobenzene
1-hydroxy-2-amino-4,6-dinitrobenzene
1-β-hydroxyethyloxy-2-β-hydroxyethylamino-5-nitrobenzene
1-methoxy-2-β-hydroxyethylamino-5-nitrobenzene
1-β-hydroxyethyloxy-3-methylamino-4-nitrobenzene
1-β,γ-dihydroxypropyloxy-3-methylamino-4-nitrobenzene
1-β-hydroxyethylamino-4-β,γ-dihydroxypropyloxy-2-nitrobenzene
1-β,γ-dihydroxypropylamino-4-trifluoromethyl-2-nitrobenzene
1-β-hydroxyethylamino-4-trifluoromethyl-2-nitrobenzene
1-β-hydroxyethylamino-3-methyl-2-nitrobenzene
1-β-aminoethylamino-5-methoxy-2-nitrobenzene
1-hydroxy-2-chloro-6-ethylamino-4-nitrobenzene
1-hydroxy-2-chloro-6-amino-4-nitrobenzene
1-hydroxy-6-bis(β-hydroxyethyl)amino-3-nitrobenzene
1-β-hydroxyethylamino-2-nitrobenzene
1-hydroxy-4-β-hydroxyethylamino-3-nitrobenzene.

Among the azo direct dyes, mention may be made of the cationic azo dyes described in patent applications WO 95/15144, WO 95/01772 and EP-714954, the contents of which are incorporated herein by reference. Among these compounds, mention may be made, for example, of the following dyes:

1,3-dimethyl-2-[[4-(dimethylamino)phenyl]azo]-1H-imidazolium chloride,
1,3-dimethyl-2-[(4-aminophenyl)azo]-1H-imidazolium chloride, and
1-methyl-4-[(methylphenylhydrazono)methyl]pyridinium methyl sulphate.

Among the azo direct dyes, examples include the following dyes, described in the COLOUR INDEX INTERNATIONAL, 3rd edition:

Disperse Red 17
Acid Yellow 9
Acid Black 1
Basic Red 22
Basic Red 76
Basic Yellow 57
Basic Brown 16
Acid Yellow 36
Acid Orange 7
Acid Red 33
Acid Red 35
Basic Brown 17
Acid Yellow 23
Acid Orange 24
Disperse Black 9.

Further examples of azo direct dyes include 1-(4'-aminodiphenylazo)-2-methyl-4-bis(β-hydroxyethyl)aminobenzene and 4-hydroxy-3-(2-methoxyphenylazo)-1-naphthalenesulphonic acid.

Among the quinone direct dyes, examples include the following dyes:

Disperse Red 15
Solvent Violet 13
Acid Violet 43
Disperse Violet 1
Disperse Violet 4
Disperse Blue 1
Disperse Violet 8
Disperse Blue 3

Disperse Red 11
Acid Blue 62
Disperse Blue 7
Basic Blue 22
Disperse Violet 15
Basic Blue 99 and further examples include the following compounds:

1-N-methylmorpholiniumpropylamino-4-hydroxyanthraquinone
1-aminopropylamino-4-methylaminoanthraquinone
1-aminopropylaminoanthraquinone
5-β-hydroxyethyl-1,4-diaminoanthraquinone
2-aminoethylaminoanthraquinone
1,4-bis(β,γ-dihydroxypropylamino)anthraquinone.

Among the azine direct dyes, examples include the following compounds:

Basic Blue 17
Basic Red 2.

Among the triarylmethane direct dyes, examples include:

Basic Green 1
Acid Blue 9
Basic Violet 3
Basic Violet 14
Basic Blue 7
Acid Violet 49
Basic Blue 26
Acid Blue 7.

Among the indoamine direct dyes, examples include the following compounds:

2-β-hydroxyethylamino-5-[bis(β-4'-hydroxyethyl )amino]anilino-1,4-benzoquinone
2-β-hydroxyethylamino-5-(2'-methoxy-4'-amino)anilino-1,4-benzoquinone
3-N-(2'-chloro-4'-hydroxy)phenylacetylamino-6-methoxy-1,4-benzoquinoneimine
3-N-(3'-chloro-4'-methylamino)phenylureido-6-methyl-1,4-benzoquinoneimine
3-[4'-N-(ethylcarbamylmethyl)amino]phenylureido-6-methyl-1,4-benzoquinoneimine.

Among the natural direct dyes, examples include lawsone, juglone, alizarin, purpurin, carminic acid, kermesic acid, purpurogallin, protocatechaldehyde, indigo, isatin, curcumin, spinulosin, and apigenidin. It is also possible to use extracts or decoctions comprising these natural dyes, such as henna-based poultices or extracts.

The at least one additional direct dye is present, for example, in an amount ranging from about 0.001% to about 20% by weight of the total weight of the composition, and, for example, from about 0.005% to about 10% by weight relative to the total weight of the composition.

The composition of the invention may further comprise at least one oxidizing agent. Such oxidizing agent may be any oxidizing agent used conventionally for bleaching human keratin fibres. The oxidizing agent may be chosen from, for example, hydrogen peroxide, urea peroxide, alkali metal bromates, persalts such as perborates and persulphates, peracids and enzymes, among which mention may be made, for example, of peroxidases, 2-electron oxidoreductases such as uricases, and 4-electron oxygenases such as laccases.

When the composition according to the invention is intended for conventional oxidation dyeing, it further comprises at least one oxidation base. Such oxidation base may be chosen from the oxidation bases conventionally used in oxidation dyeing, for example para-phenylenediamines, bisphenylalkylenediamines, para-aminophenols, ortho-aminophenols, and heterocyclic bases.

Among the para-phenylenediamines, mention may be made, for example, of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-pheylenediamine, 4-amino-N,N-bis(β-hydroxyethyl)-2-methylaniline, 4-amino-2-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(-β,γdihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenyl-pyrrolidone, 2-thienyl-para-phenylenediamine, and 5-amino-2-β-hydroxyethylaminotoluene, and the acid addition salts thereof.

Among the para-phenylenediamines, mention may also be made, for example, of para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, and 2-β-acetylaminoethyloxy-para-phenylenediamine, and the acid addition salts thereof.

Among the bisphenylalkylenediamines, mention may be made, for example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-amino-phenyl)tetramethylenediamine, N,N'-bis(4-methylaminophenyl)tetramethylenediamine, N,N'-bis(ethyl)-N,N'-bis(4'-amino-3'-methylphenyl)ethylenediamine, and 1,8-bis(2,5-diaminophenoxy)-3,6-dioxaoctane, and the acid addition salts thereof.

Among the para-aminophenols, mention may be made, for example, of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, and 4-amino-2-fluorophenol, and the acid addition salts thereof.

Among the ortho-aminophenols, mention may be made, for example, of 2-aminophenol, 2-amino-5-methylphenol, 2-amino-6-methylphenol, and 5-acetamido-2-aminophenol, and the acid addition salts thereof.

Among the heterocyclic bases, mention may be made, for example, of pyridine derivatives, pyrimidine derivatives, and pyrazole derivatives.

Among the pyridine derivatives, mention may be made, for example, of compounds described in patents GB 1 026 978 and GB 1 153 196, incorporated herein by reference, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, and 3,4-diaminopyridine, and the acid addition salts thereof.

Among the pyrimidine derivatives, mention may be made, for example, of compounds described, in patents DE 2 359 399; JP 88-169 571; JP 05 163 124; and EP 0 770 375 and patent application WO 96/15765, incorporated herein by reference, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, and 2,5,6-triaminopyrimidine, and the pyrazolopyrimidine derivatives such as those mentioned in patent application FR-A-2 750 048, and further, for example, pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, and 3-amino-5-methyl-7-imidazolylpropyl-aminopyrazolo[1,5-a]pyrimidine, and the acid addition salts thereof, and the tautomeric forms thereof, when a tautomeric equilibrium exists.

Among the pyrazole derivatives, mention may be made, for example, of compounds described in DE 3 843 892 and DE 4 133 957, and patent applications WO 94/08969, WO 94/08970, FR-A-2 733 749, and DE 195 43 988 incorporated herein by reference, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenyl-pyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, and 3,5-diamino-4-(β-hydroxyethyl)amino-1-methylpyrazole, and the acid addition salts thereof.

The composition according to the invention may further comprise at least one coupler conventionally used for the conventional oxidation dyeing of human keratin fibres, such as hair. Among those conventionally used couplers, mention may be made, for example, of meta-phenylenediamines, meta-aminophenols, meta-diphenols, naphthalene couplers, and heterocyclic couplers.

Examples include 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, and 2,6-bis(β-hydroxyethylamino)toluene, and the acid addition salts thereof.

In the composition of the present invention, the at least one coupler is generally present in an amount, for example, ranging from about 0.001% to about 10% by weight of the total weight of the dye composition, and further, for example, ranging from about 0.005% to about 6% by weight of the total weight of the dye composition. The at least one oxidation base is present, for example, in an amount ranging from about 0.001% to about 10% by weight of the total weight of the dye composition, and further, for example, ranging from about 0.005% to about 6% by weight of the total weight of the dye composition.

In general, the acid addition salts that can be used in the context of the dye compositions of the invention for the oxidation bases and the couplers, may be chosen from, for example, hydrochlorides, hydrobromides, sulphates, citrates, succinates, tartrates, lactates, tosylates, benzenesulphonates, phosphates, and acetates.

The cosmetically acceptable medium, also referred to as dye support, generally consists of water or of a mixture of water and at least one organic solvent in order to solubilize the compounds, which would not be sufficiently water-soluble. For the organic solvent, mention may be made, for example, of $C_1$–$C_4$ lower alkanols such as ethanol and isopropanol; polyols and polyol ethers such as 2-butoxyethanol, propylene glycol, propylene glycol monomethyl ether, diethylene glycol monoethyl ether, and monomethyl ether; and aromatic alcohols such as benzyl alcohol and phenoxyethanol, and mixtures thereof.

The at least one organic solvent may be present in an amount ranging, for example, from about 1% to about 40% by weight relative to the total weight of the dye composition, and further, for example, from about 5% to about 30% by weight relative to the total weight of the dye composition.

The dye composition in accordance with the invention may further comprise at least one adjuvant chosen from various adjuvants used conventionally in compositions for dyeing hair, such as anionic, cationic, nonionic, amphoteric, and zwitterionic surfactants, and mixtures thereof; anionic, cationic, nonionic, amphoteric, and zwitterionic polymers, and mixtures thereof; inorganic and organic thickeners, and for example, thickeners combining anionic, cationic, nonionic, and amphoteric polymers; antioxidants; penetration agents; sequestering agents; fragrances; buffers; dispersing agents; conditioners, such as, for example, volatile and non-volatile silicones, which are modified or unmodified; film-forming agents; ceramides; preserving agents; and opacifiers.

The at least one adjuvant may generally be present in an amount, for example, ranging from about 0.01% to about 20% by weight relative to the total weight of the composition.

Of course, those skilled in the art will take care to select these optional additional compounds such that the advantageous properties intrinsically associated with the dye composition in accordance with the invention are not, or are not substantially, adversely affected by the addition envisaged.

The pH of the dye composition in accordance with the invention is generally ranging, for example, from about 3 to about 12, and, further for example, from about 5 to about 11. It may be adjusted to the desired value by means of acidifying or basifying agents conventionally used in dyeing keratin fibres, or by using conventional buffer systems.

Among the acidifying agents, mention may be made, for example, of inorganic and organic acids such as hydrochloric acid, orthophosphoric acid, and sulphuric acid; carboxylic acids such as acetic acid, tartaric acid, citric acid and lactic acid; and sulphonic acids.

Among the basifying agents, mention may be made, for example, of aqueous ammonia, alkaline carbonates, alkanolamines such as mono-, di- and triethanolamines, and derivatives thereof, sodium hydroxide, and potassium hydroxide, and the compounds of formula (V) below:

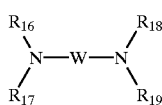

(V)

wherein:

W is chosen from propylene residues optionally substituted with a radical chosen from hydroxyl and $C_1$–$C_4$ alkyl radicals; $R_{16}$, $R_{17}$, $R_{18}$ and $R_{19}$, which may be identical or different, are each chosen from a hydrogen atom, $C_1$–$C_4$ alkyl radicals, and $C_1$–$C_4$ hydroxyalkyl radicals.

The dye composition according to the invention may be in various forms, such as liquids, creams, gels, or in any other form which is suitable for dyeing human keratin fibres, such as hair.

Another aspect of the invention relates to a direct dyeing process, which comprises applying to human keratin fibres, such as hair, a dye composition comprising a dye of formula (I) as defined above; leaving the dye composition standing on the human keratin fibres for a period of time; rinsing the human keratin fibres; and allowing coloured fibres to appear.

In one embodiment, the dye composition comprising the dye of formula (I) may be applied to the fibres in the presence of oxidizing agent, which may cause bleaching of the fibre (direct lightening dyeing). This oxidizing agent may be added to the composition comprising at least one monocationic monoazo dye of formula (I) at the time of use, or directly to the fibre.

Another aspect of the invention is an oxidation dyeing process, which comprises applying a dye composition, comprising at least one dye of formula (I), at least one oxidation base and, optionally, at least one coupler, to human keratin fibres, in the presence of at least one oxidizing agent. The oxidation base, the coupler, and the oxidizing agent are as defined above.

The colour may be developed at acidic, neutral or alkaline pH, and the oxidizing agent may be added to the composition of the invention just at the time of use, or it may be used as an ingredient of an oxidizing composition and applied to the fibres simultaneously with, or sequentially to, the dye composition.

In the case of oxidation dyeing or of direct dyeing, the dye composition may be mixed, for example, at the time of use, with a composition comprising, in a medium which is suitable for dyeing, at least one oxidizing agent, such oxidizing agent being present in an amount sufficient to develop a coloration. The mixture obtained is then applied to the fibres. After a period ranging from about 3 to about 50 minutes, and for example from about 5 to about 30 minutes, in which the mixture is left on the fibres, the fibres are rinsed, washed with shampoo, rinsed again, and then dried.

The oxidizing composition of the present invention may also comprise various adjuvants conventionally used in compositions for dyeing the hair, and as defined above.

The pH of the oxidizing composition comprising at least one oxidizing agent is such that, after mixing with the dye composition, the pH of the resulting composition that is applied to the keratin fibres ranges, for example, from about 3 to about 12, and further for example, from about 5 to about 11. The pH may be adjusted to the desired value by means of acidifying or basifying agents conventionally used in dyeing human keratin fibres, such as those defined above.

The composition which is finally applied to the fibres may be in various forms, such as liquids, creams, gels, or in any other form which is suitable for dyeing human keratin fibres, such as hair.

Another aspect of the invention is a multicompartment device or dyeing "kit" in which a first compartment comprises the dye composition of the invention and a second compartment comprises the oxidizing composition. This device may be equipped with a means for applying the desired mixture to the hair, such as the devices described in patent FR-2 586 913.

Yet another aspect of the invention is also the novel monocationic monoazo compounds of formula (I) as defined above wherein, in formula (II), n is chosen from 0, 2, and 3.

Another aspect of the invention is also the addition of the monocationic monoazo dyes of formula (I), as direct dyes, in a composition for dyeing human keratin fibres, such as hair, as well as a method of preparation thereof.

The compounds of the invention may be obtained conventionally from a diazonium salt of 2-aminobenzimidazole. The diazonium preparation is known and described in the literature, and it is carried out in a dilute hydrochloric acid medium.

The diazonium salt is then condensed with a compound from the family of the cyclic N,N-dialkyls of anilines, in the presence of an organic base.

At the end of this condensation, the reaction medium is brought back to basic pH and the azo compound thus formed is isolated.

The azo compound thus obtained is quaternized in a solvent at a temperature ranging from 40° C. to 140° C. using an alkylating agent.

Thus, for example, the 2-aminobenzimidazole derivatives react with sodium nitrite in an acid medium to produce the diazonium reactive intermediate, which, itself, is reacted with a cyclic aniline derivative. The preparations are known and fully described in U.S. Pat. Nos. 5,208,325 and 5,436,323. The protocol is also applied to 2-aminobenzoxazole and 2-aminobenzothiazole derivatives.

The corresponding azo compounds are then quaternized with the halides $R_{13}$—X according to the following reaction scheme:

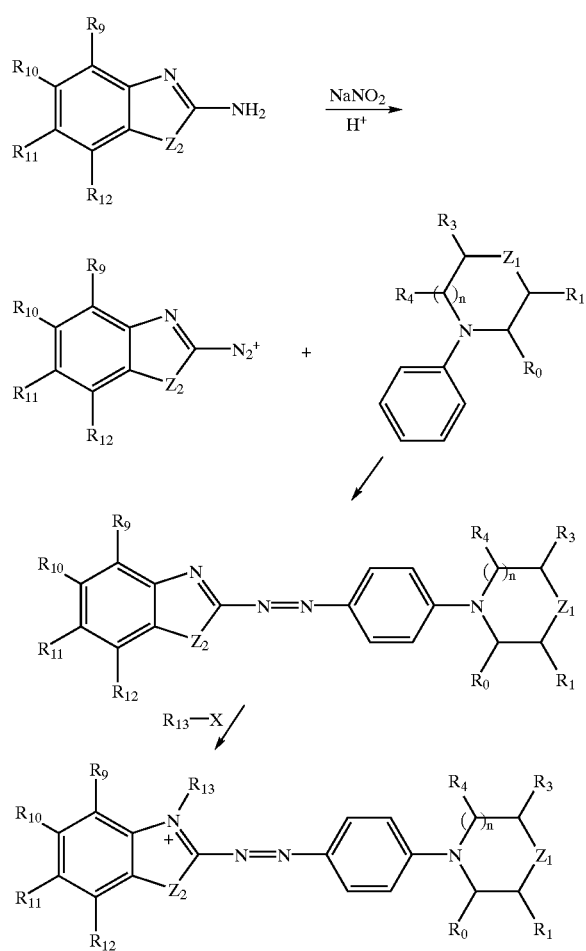

The corresponding monocationic monoazo dyes of formula (I) may be obtained by applying the same synthetic process to pyridine derivatives and pyridazine derivatives substituted with a cyclic amine comprising 5 to 8 ring members.

The examples which follow serve to illustrate the invention without, however, being limiting in nature.

EXAMPLE OF SYNTHESIS

The compound in accordance with the invention, with the following formula, was prepared:

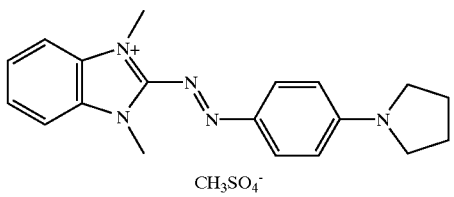

First Stage

Synthesis of (1H-benzoimidazol-2-yl)-(4-pyrrolidin-1-ylphenyl)diazene of formula:

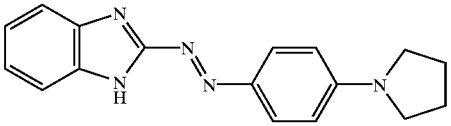

5.42 g ($4 \times 10^{-2}$ mol) of 2-aminobenzimidazole were solubilized in 400 ml of orthophosphoric acid in a fully equipped round-bottomed flask.

After cooling to 0° C., a solution of sodium nitride (3.92 g in 20 ml of water) was run in over 30 minutes, and the mixture was then stirred for 15 minutes.

Next, 1.5 kg of ice were added over 30 minutes with stirring.

An ethanolic solution of 1-phenylpyrrolidine (5.4 g in 20 ml of ethanol) was then added dropwise for 30 minutes.

At 0° C., the pH of the medium was brought back to 7 with an aqueous ammonia solution and the brick-red product formed was filtered off over a No. 4 sintered glass funnel and then washed with 10 times 100 ml of water. After drying, 2 grams of brick-red product were recovered.

Second Stage

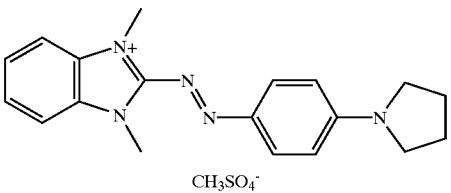

1.51 g ($5.2 \times 10^{-3}$ mol) of (1H-benzoimidazol-2-yl)-(4-pyrrolidin-1-ylphenyl)diazene obtained as described above, 10 ml of anhydrous dichloroethane, 1.4 g ($10^{-3}$ mol) of sodium acetate and 1.08 ml of dimethyl sulphate were introduced into a fully equipped round-bottomed flask.

The mixture was brought to 50° C. for 1 hour and 30 minutes with stirring. The solid was filtered off, washed with dichloroethane and then dried. 2.08 g of dark violet powder were obtained, having the following UV absorption characteristics:

UV (ethanol) $\lambda_{max}$=576 nm $\epsilon_{max}$=30 000 L·mol$^{-1}$ cm$^{-1}$ 1H NMR: (400 MHz-DMSO) ppm: standard

Example of Application

A dye composition comprising 1.25 grams of dye prepared in the previous example, 13 grams of an aqueous ammonia solution comprising 40% of ammonia by weight, and demineralised water q.s. for 100 grams was mixed at the time of use with a 20-volumes aqueous hydrogen peroxide composition, in a proportion of 1 part dye composition for 1.5 parts oxidizing composition. The mixture obtained was applied to locks of natural and permanent-waved hair comprising 90% white hairs (1 gram of hair per 10 grams of mixture).

The composition was left to stand on the locks of hair for 35 minutes at ambient temperature.

The locks were then rinsed with water, shampooed and then dried.

They were dyed in a shade of iridescent deep purple to deep purple very resistant to light.

What is claimed is:

1. A cosmetic composition for dyeing human keratin fibres comprising, in a cosmetically acceptable medium, at least one monocationic monoazo dye of formula (I) below:

$W_1$—$W_2$—N=N—$W_3$   Formula (I)

wherein:

$W_1$ is chosen from 5-, 6-, 7- and 8-membered heterocycles of formula (II) below:

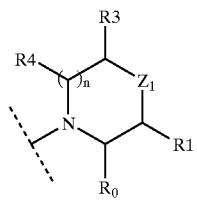

Formula (II)

$W_2$ is chosen from divalent, aromatic, and carbon-based pyridines and pyridazines of formula (III) below:

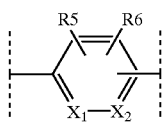

Formula (III)

$W_3$ is chosen from cationic heteroaromatic radicals of formula (IV) below:

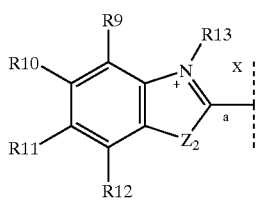

(IV)

wherein in formulae (II), (III) and (IV):

n=0, 1, 2 or 3, provided that when n is greater than or equal to 2, then the $R_4$ radicals may be identical or different, $X_1$ is chosen from a nitrogen atom and $CR_7$ radicals, $X_2$ is chosen from a nitrogen atom and $CR_8$ radicals, $Z_1$ is chosen from $CHR_2$ radicals, oxygen and sulphur atoms, and $NR_{14}$ radicals, $Z_2$ is chosen from oxygen and sulphur atoms, and $NR_{15}$ radicals, $R_0$, $R_1$, $R_2$, $R_3$, $R_4$, $R_5$, $R_6$, $R_7$, $R_8$, $R_9$, $R_{10}$, $R_{11}$ and $R_{12}$, which may be identical or different, are each chosen from a hydrogen atom, linear and branched $C_1$–$C_{10}$ hydrocarbon-based chains, possibly forming at least one carbon-based ring comprising from 3 to 6 members, and being saturated or unsaturated, wherein at least one carbon atom of the hydrocarbon-based chains may be replaced with an entity chosen from oxygen, nitrogen, and sulphur atoms, and an $SO_2$ group, and wherein the carbon atoms may be, independently of one another, substituted; $R_0$, $R_1$, $R_2$, $R_3$, $R_4$, $R_5$, $R_6$, $R_7$, $R_8$, $R_9$, $R_{11}$ and $R_{12}$ comprising no peroxide bond, nor any diazo or nitroso radicals, $R_{14}$ is chosen from a hydrogen atom, linear and branched $C_1$–$C_{10}$ hydrocarbon-based chains, possibly forming at least one carbon-based ring comprising from 3 to 6 members, and being saturated or unsaturated, wherein at least one carbon atom of the hydrocarbon-based chains may be replaced with an entity chosen from oxygen, nitrogen, and sulphur atoms, and an $SO_2$ group, and wherein the carbon atoms may be, independently of one another, substituted, $R_{14}$ comprising no peroxide bond, nor any diazo or nitroso radicals; provided that said oxygen, nitrogen and sulphur atoms are not linked directly to the nitrogen atom carrying the $R_{14}$ radical, $R_5$ with $R_6$ may optionally form a carbon-based aromatic ring, $R_{13}$ and $R_{15}$, which may be identical or different, are each chosen from $C_1$–$C_8$ alkyl radicals optionally substituted with at least one radical chosen from hydroxyl, $C_1$–$C_2$ alkoxy, $C_2$–$C_4$ (poly)hydroxyalkoxy, unsubstituted and substituted amino, carboxyl, sulphonic, and phenyl radicals, which are optionally substituted;

the bond a of the cationic ring of formula (IV) is linked to the azo group of formula (I);

X is an anion chosen from organic and inorganic anions.

2. The composition according to claim 1, wherein said human keratin fibres are hair, wherein the carbon atoms may be, independently of one another, substituted with at least one halogen atom, both for $R_0$ to $R_{12}$ and for $R_{14}$, and further wherein for $R_{13}$ and $R_{15}$, said unsubstituted and substituted amino radicals are chosen from unsubstituted amino and $C_1$–$C_2$ (di)alkylamino.

3. The composition according to claim 1, wherein, in formula (I), $R_1$, $R_2$, and $R_3$, which may be identical or different, are each chosen from a hydrogen atom; alkoxy, hydroxyl, substituted and unsubstituted amino, and acetoxy radicals; linear and branched $C_1$–$C_4$ alkyl radicals substituted with at least one substituent chosen from halogen atoms, hydroxyl, $C_1$–$C_2$ alkoxy, (poly)hydroxyalkoxy, unsubstituted amino, $C_1$–$C_2$ (di)alkylamino, carboxyl, and sulphonic radicals; and —$NR_{16}R_{17}$ groups, wherein $R_{16}$ and $R_{17}$, which may be identical or different, are each chosen from a hydrogen atom, methylsulphonyl, carboxyl, carboxamido, and $C_1$–$C_4$ alkyl radicals substituted with at least one substituent chosen from halogen atoms, hydroxyl, $C_1$–$C_2$ alkoxy, unsubstituted amino, $C_1$–$C_2$ (di)alkylamino, and carboxyl radicals.

4. The composition according to claim 3, wherein $R_1$, $R_2$ and $R_3$, which may be identical or different, are each chosen from a hydrogen atom; a hydroxyl radical; amino radicals which are optionally mono- or disubstituted; linear and branched $C_1$–$C_3$ alkyl radicals optionally substituted with at least one radical chosen from hydroxyl, $C_1$–$C_2$ alkoxy, unsubstituted amino, $C_1$–$C_2$ (di)alkylamino, carboxyl and sulphonic radicals.

5. The composition according to claim 4, wherein $R_1$, $R_2$ and $R_3$, which may be identical or different, are each chosen from a hydrogen atom, a methyl radical, a hydroxyl radical, an unsubstituted amino radical, a (di)methylamino radical, a methylsulphonylamino radical, $C_2$–$C_4$ (poly)hydroxyalkylamino radicals, and a hydroxymethyl radical.

6. The composition according to claim 1, wherein $R_1$ in formula (II) is chosen from a hydrogen atom, and methyl, hydroxyl, unsubstituted amino, methylamino, dimethylamino and 2-hydroxyethylamino radicals.

7. The composition according to claim 6, wherein $R_1$ in formula (II) is chosen from a hydrogen atom, and hydroxyl, unsubstituted amino, and dimethylamino radicals.

8. The composition according to claim 7, wherein $R_1$ in formula (II) is chosen from a hydrogen atom, and a hydroxyl radical.

9. The composition according claim 1, wherein $R_0$ in formula (II) is chosen from a hydrogen atom, and linear and branched $C_1$–$C_4$ alkyl radicals substituted with at least one radical chosen from hydroxyl, methoxy, unsubstituted amino, (di)alkylamino, carboxyl, sulphonyl, amido, and dimethylamido radicals.

10. The composition according claim 1, wherein $R_0$ in formula (II) is chosen from a hydrogen atom, and carboxyl, amido, dimethylamido, and hydroxymethyl radicals.

11. The composition according claim 10, wherein $R_0$ in formula (II) is a hydrogen atom.

12. The composition according to claim 1, wherein $Z_1$ in formula (II) is chosen from $NR_{14}$ radicals and $CHR_2$ radicals.

13. The composition according to claim 12, wherein $Z_1$ in formula (II) is chosen from $CHR_2$ radicals.

14. The composition according to claim 12, wherein $Z_1$ in formula (II) is chosen from $CH_2$, CHOH, $CHNH_2$, and $CHN(CH_3)_2$.

15. The composition according to claim 14, wherein $Z_1$ in formula (II) is $CH_2$.

16. The composition according to claim 1, wherein n in formula (II) is chosen from 0 and 1.

17. The composition according to claim 16, wherein n in formula (II) is 0.

18. The composition according to claim 1, wherein $R_5$, $R_6$, $R_7$, $R_8$, $R_9$, $R_{10}$, $R_{11}$ and $R_{12}$, which may be identical or different, are each chosen from a hydrogen atom, and methyl, ethyl, isopropyl, methoxymethyl, hydroxymethyl, 1-carboxymethyl, 1-aminomethyl, 2-carboxyethyl, 2-hydroxyethyl, 3-hydroxypropyl, 1,2-dihydroxyethyl, 1-hydroxy-2-aminoethyl, 2-hydroxy-1-aminoethyl, methoxy, ethoxy, 2-hydroxyethyloxy, 3-aminoethyloxy, unsubstituted amino, methylamino, dimethylamino, and 2-hydroxyethylamino radicals.

19. The composition according to claim 18, wherein $R_5$, $R_6$, $R_7$, $R_8$, $R_9$, $R_{10}$, $R_{11}$ and $R_{12}$, which may be identical or different, are each chosen a hydrogen atom, and methyl, hydroxymethyl, 2-hydroxyethyl, 1,2-dihydroxyethyl, methoxy, 2-hydroxyethyloxy, unsubstituted amino, and 2-hydroxyethylamino radicals.

20. The composition according to claim 19, wherein $R_5$, $R_6$, $R_7$, $R_8$, $R_9$, $R_{10}$, $R_{11}$ and $R_{12}$, which may be identical or different, are each chosen from a hydrogen atom, and methyl, methoxy, and unsubstituted amino radicals.

21. The composition according to claim 1, wherein said carbon-based aromatic ring optionally formed by $R_5$ with $R_6$ is phenyl.

22. The composition according to claim 1, wherein $X_1$ in formula (III) is chosen from $CR_7$ radicals, wherein $R_7$ is chosen from a hydrogen atom, and methyl, ethyl, isopropyl, methoxymethyl, hydroxymethyl, 1-carboxymethyl, 1-aminomethyl, 2-carboxyethyl, 2-hydroxyethyl, 3-hydroxypropyl, 1,2-dihydroxyethyl, 1-hydroxy-2-aminoethyl, 2-hydroxy-1-aminoethyl, methoxy, ethoxy, 2-hydroxyethyloxy, 3-aminoethyloxy, unsubstituted amino, methylamino, dimethylamino, and 2-hydroxyethylamino radicals.

23. The composition according to claim 1, wherein $X_2$ in formula (III) is chosen from $CR_8$ radicals, wherein $R_8$ is chosen from a hydrogen atom, and methyl, ethyl, isopropyl, methoxymethyl, hydroxymethyl, 1-carboxymethyl, 1-aminomethyl, 2-carboxyethyl, 2-hydroxyethyl, 3-hydroxypropyl, 1,2-dihydroxyethyl, 1-hydroxy-2-aminoethyl, 2-hydroxy-1-aminoethyl, methoxy, ethoxy, 2-hydroxyethyloxy, 3-aminoethyloxy, unsubstituted amino, methylamino, dimethylamino, and 2-hydroxyethylamino radicals.

24. The composition according to claim 1, wherein $R_{13}$ and $R_{15}$, which may be identical or different, are each chosen from $C_1$–$C_4$ alkyl radicals optionally substituted with at least one radical chosen from hydroxyl, $C_1$–$C_2$ alkoxy, unsubstituted amino, $C_1$–$C_2$ (di)alkylamino, carboxyl, sulphonic, and phenyl radicals.

25. The composition according to claim 24, wherein $R_{13}$ and $R_{15}$, which may be identical or different, are each chosen from methyl, ethyl, 2-hydroxyethyl, 1-carboxymethyl, 2-carboxyethyl, and 2-sulphonylethyl radicals.

26. The composition according to claim 24, wherein $R_{13}$ and $R_{15}$, which may be identical or different, are each chosen from $C_1$–$C_3$ alkyl radicals optionally substituted with at least one radical chosen from hydroxyl, methoxy, unsubstituted amino, dimethylamino, carboxyl, and sulphonic radicals.

27. The composition according to claim 26, wherein $R_{13}$ and $R_{15}$, which may be identical or different, are each chosen from methyl, ethyl, 2-hydroxyethyl, and carboxy-methyl radicals.

28. The composition according to claim 27, wherein $R_{13}$ and $R_{15}$ are each a methyl radical.

29. The composition according to claim 12, wherein $Z_1$ is chosen from $NR_{14}$ radicals, wherein $R_{14}$ is chosen from a hydrogen atom, and linear and branched $C_1$–$C_3$ alkyl radicals optionally substituted with at least one radical chosen from hydroxyl, methoxy, unsubstituted amino, methylamino, dimethylamino, carboxyl, and sulphonyl radicals.

30. The composition according to claim 29, wherein $R_{14}$ is chosen from a hydrogen atom, and methyl and 2-hydroxyethyl radicals.

31. The composition according to claim 1, wherein $Z_2$ in formula (IV) is chosen from $NR_{15}$ radicals, wherein $R_{15}$ is chosen from $C_1$–$C_4$ alkyl radicals optionally substituted with at least one radical chosen from hydroxyl, $C_1$–$C_2$ alkoxy, unsubstituted amino, $C_1$–$C_2$ (di)alkylamino, carboxyl, sulphonic, and phenyl radicals.

32. A cosmetic composition for dyeing human keratin fibres comprising, in a cosmetically acceptable medium, at least one dye chosen from:

1,3-dimethyl-2-[4-(pyrrolidin-1-yl)phenylazo] benzimidazol-1-ium, 1,3-dimethyl-2-[4-(3-hydroxypyrrolidin-1-yl)phenylazo] benzimidazol-1-ium, 1,3-dimethyl-2-[4-(2-carboxypyrrolidin-1-yl)phenylazo] benzimidazol-1-ium, 1,3-dimethyl-2-[4-(3-aminopyrrolidin-1-yl)phenylazo] benzimidazol-1-ium, 1,3-dimethyl-2-[4-(2-carboxy-3-hydroxypyrrolidin-1-yl) phenylazo]benzimidazol-1-ium, 1,3-dimethyl-2-[4-(2-carboxamidopyrrolidin-1-yl) phenylazo]benzimidazol-1-ium, 1,3-dimethyl-2-[4-(2-hydroxymethylpyrrolidin-1-yl) phenylazo]benzimidazol-1-ium, 1,3-dimethyl-2-[4-(2-carboxy-4-hydroxypyrrolidin-1-yl) phenylazo]benzimidazol-1-ium, 1,3-dimethyl-2-[4-(piperidin-1-yl)phenylazo] benzimidazol-1-ium, 1,3-dimethyl-2-[4-(3-hydroxypiperidin-1-yl)phenylazo] benzimidazol-1-ium, 1,3-dimethyl-2-[4-(3-hydroxymethylpiperidin-1-yl) phenylazo]benzimidazol-1-ium, 1,3-dimethyl-2-[4-(3-carboxypiperidin-1-yl)phenylazo]benzimidazol-1-ium, 1,3-dimethyl-2-[4-(2-carboxypiperidin-1-yl)phenylazo]benzimidazol-1-ium, 1,3-dimethyl-2-[4-(piperazin-1-yl)phenylazo]benzimidazol-1-ium, 1,3-dimethyl-2-[4-(homopiperazin-1-yl)phenylazo]benzimidazol-1-ium, 5-amino-1,3-dimethyl-2-[4-(pyrrolidin-1-yl)phenylazo]benzimidazol-1-ium, 5-amino-1,3-dimethyl-2-[4-(3-hydroxypyrrolidin-1-yl)phenylazo]benzimidazol-1-ium, 5-amino-1,3-dimethyl-2-[4-(2-carboxypyrrolidin-1-yl)phenylazo]benzimidazol-1-ium, 5-amino-1,3-dimethyl-2-[4-(3-aminopyrrolidin-1-yl)phenylazo]benzimidazol-1-ium, 5-amino-1,3-dimethyl-2-[4-(2-carboxy-3-hydroxypyrrolidin-1-yl)phenylazo]benzimidazol-1-ium, 5-amino-1,3-dimethyl-2-[4-(2-carboxamidopyrrolidin-1-yl)phenylazo]benzimidazol-1-ium, 5-amino-1,3-dimethyl-2-[4-(2-hydroxymethylpyrrolidin-1-yl)phenylazo]benzimidazol-1-ium, 5-amino-1,3-dimethyl-2-[4-(2-carboxy-4-hydroxypyrrolidin-1-yl)phenylazo]benzimidazol-1-ium, 5-amino-1,3-dimethyl-2-[4-(piperidin-1-yl)phenylazo]benzimidazol-1-ium, 5-amino-1,3-dimethyl-2-[4-(3-hydroxypiperidin-1-yl)phenylazo]benzimidazol-1-ium, 5-amino-1,3-dimethyl-2-[4-(3-hydroxymethylpiperidin-1-yl)phenylazo]benzimidazol-1-ium, 5-amino-1,3-dimethyl-2-[4-(3-carboxypiperidin-1-yl)phenylazo]benzimidazol-1-ium, 5-amino-1,3-dimethyl-2-[4-(2-carboxypiperidin-1-yl)phenylazo]benzimidazol-1-ium, 5-amino-1,3-dimethyl-2-[4-(piperazin-1-yl)phenylazo]benzimidazol-1-ium, 5-amino-1,3-dimethyl-2-[4-(homopiperazin-1-yl)phenylazo]benzimidazol-1-ium, 5-dimethylamino-1,3-dimethyl-2-[4-(pyrrolidin-1-yl)phenylazo]benzimidazol-1-ium, 5-dimethylamino-1,3-dimethyl-2-[4-(3-hydroxypyrrolidin-1-yl)phenylazo]benzimidazol-1-ium, 5-dimethylamino-1,3-dimethyl-2-[4-(2-carboxypyrrolidin-1-yl)phenylazo]benzimidazol-1-ium, 5-dimethylamino-1,3-dimethyl-2-[4-(3-aminopyrrolidin-1-yl)phenylazo]benzimidazol-1-ium, 5-dimethylamino-1,3-dimethyl-2-[4-(2-carboxy-3-hydroxypyrrolidin-1-yl)phenylazo]benzimidazol-1-ium, 5-dimethylamino-1,3-dimethyl-2-[4-(2-carboxamidopyrrolidin-1-yl)phenylazo]benzimidazol-1-ium, 5-dimethylamino-1,3-dimethyl-2-[4-(2-hydroxymethylpyrrolidin-1-yl)phenylazo]benzimidazol-1-ium, 5-dimethylamino-1,3-dimethyl-2-[4-(2-carboxy-4-hydroxypyrrolidin-1-yl)phenylazo]benzimidazol-1-ium, 5-dimethylamino-1,3-dimethyl-2-[4-(piperidin-1-yl)phenylazo]benzimidazol-1-ium, 5-dimethylamino-1,3-dimethyl-2-[4-(3-hydroxypiperidin-1-yl)phenylazo]benzimidazol-1-ium, 5-dimethylamino-1,3-dimethyl-2-[4-(3-hydroxymethylpiperidin-1-yl)phenylazo]benzimidazol-1-ium, 5-dimethylamino-1,3-dimethyl-2-[4-(3-carboxypiperidin-1-yl)phenylazo]benzimidazol-1-ium, 5-dimethylamino-1,3-dimethyl-2-[4-(2-carboxypiperidin-1-yl)phenylazo]benzimidazol-1-ium, 5-dimethylamino-1,3-dimethyl-2-[4-(piperazin-1-yl)phenylazo]benzimidazol-1-ium, and 5-dimethylamino-1,3-dimethyl-2-[4-(homopiperazin-1-yl)phenylazo]benzimidazol-1-ium.

33. The composition according to claim 1, wherein X is chosen from halides, a hydroxide, a sulphate, a hydrogen sulphate, $(C_1–C_6)$ alkyl sulphates, an acetate, a tartrate, an oxalate, $(C_1–C_6)$ alkylsulphonates, and arylsulphonates which may be optionally substituted with at least one radical chosen from $C_1–C_4$ alkyl radicals.

34. The composition according to claim 1, wherein said at least one monocationic monoazo dye of formula (I) is present at a concentration ranging from about 0.001% to about 5% by weight relative to the total weight of the dye composition.

35. The composition according to claim 34, wherein said at least one monocationic monoazo dye of formula (I) is present at a concentration ranging from about 0.05% to about 2% by weight relative to the total weight of the dye composition.

36. A composition according to claim 1, further comprising at least one direct dye, which is different from those of formula (I), chosen from neutral, acidic, and cationic nitrobenzene direct dyes, neutral, acidic and cationic azo direct dyes, neutral, acidic and cationic quinone direct dyes, azine direct dyes, methine direct dyes, triarylmethane direct dyes, indoamine direct dyes, and natural direct dyes.

37. The composition according to claim 36, wherein said quinone direct dyes are chosen from anthraquinone direct dyes.

38. A composition according to claim 1, further comprising at least one oxidizing agent.

39. The composition according to claim 38, wherein said at least one oxidizing agent is hydrogen peroxide.

40. The composition according to claim 1, further comprising at least one oxidation base.

41. The composition according to claim 40, wherein said at least one oxidation base is chosen from para-phenylenediamines, bisphenylalkylenediamines, para-aminophenols, ortho-aminophenols, and heterocyclic bases, and the acid addition salts thereof.

42. The composition according to claim 1, further comprising at least one coupler.

43. The composition according to claim 42, wherein said at least one coupler is chosen from meta-phenylenediamines, meta-aminophenols, meta-diphenols, naphthalene couplers, and heterocyclic couplers, and the acid addition salts thereof.

44. A process for the direct dyeing of human keratin fibres, comprising applying to the human keratin fibres a dye composition comprising at least one monocationic monoazo dye of formula (I) below:

$$W_1—W_2—N=N—W_3 \qquad \text{Formula (I)}$$

wherein:

W$_1$ is chosen from 5-, 6-, 7- and 8-membered heterocycles of formula (II) below:

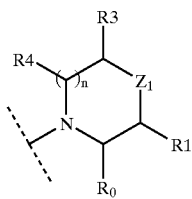

Formula (II)

W$_2$ is chosen from divalent, aromatic, and carbon-based pyridines and pyridazines of formula (III) below:

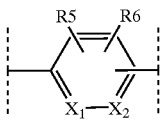

Formula (III)

W$_3$ is chosen from cationic heteroaromatic radicals of formula (IV) below:

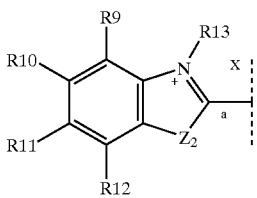

(IV)

wherein in formulae (II), (III) and (IV):

n=0, 1, 2 or 3, provided that when n is greater than or equal to 2, then the R$_4$ radicals may be identical or different, X$_1$ is chosen from a nitrogen atom and CR$_7$ radicals, X$_2$ is chosen from a nitrogen atom and CR$_8$ radicals, Z$_1$ is chosen from CHR$_2$ radicals, oxygen and sulphur atoms, and NR$_{14}$ radicals, Z$_2$ is chosen from oxygen and sulphur atoms, and NR$_{15}$ radicals, R$_0$, R$_1$, R$_2$, R$_3$, R$_4$, R$_5$, R$_6$, R$_7$, R$_8$, R$_9$, R$_{10}$, R$_{11}$ and R$_{12}$, which may be identical or different, are each chosen from a hydrogen atom, linear and branched C$_1$–C$_{10}$ hydrocarbon-based chains, possibly forming at least one carbon-based ring comprising from 3 to 6 members, and being saturated or unsaturated, wherein at least one carbon atom of the hydrocarbon-based chains may be replaced with an entity chosen from oxygen, nitrogen, and sulphur atoms, and an SO$_2$ group, and wherein the carbon atoms may be, independently of one another, substituted; R$_0$, R$_1$, R$_2$, R$_3$, R$_4$, R$_5$, R$_6$, R$_7$, R$_8$, R$_9$, R$_{11}$ and R$_{12}$ comprising no peroxide bond, nor any diazo or nitroso radicals, R$_{14}$ is chosen from a hydrogen atom, linear and branched C$_1$–C$_{10}$ hydrocarbon-based chains, possibly forming at least one carbon-based ring comprising from 3 to 6 members, and being saturated or unsaturated, wherein at least one carbon atom of the hydrocarbon-based chains may be replaced with an entity chosen from oxygen, nitrogen, and sulphur atoms, and an SO$_2$ group, and wherein the carbon atoms may be, independently of one another, substituted, R$_{14}$ comprising no peroxide bond, nor any diazo or nitroso radicals; provided that said oxygen, nitrogen and sulphur atoms are not linked directly to the nitrogen atom carrying the R$_{14}$ radical, R$_5$ with R$_6$ may optionally form a carbon-based aromatic ring, R$_{13}$ and R$_{15}$, which may be identical or different, are each chosen from C$_1$–C$_8$ alkyl radicals optionally substituted with at least one radical chosen from hydroxyl, C$_1$–C$_2$ alkoxy, C$_2$–C$_4$ (poly)hydroxyalkoxy, unsubstituted and substituted amino, carboxyl, sulphonic, and phenyl radicals, which are optionally substituted;

the bond a of the cationic ring of formula (IV) is linked to the azo group of formula (I);

X is an anion chosen from organic and inorganic anions.

45. The process according to claim 44, wherein said human keratin fibres are hair.

46. The process according to claim 45, wherein said dye composition further comprises at least one oxidizing agent.

47. The process according to claim 46, wherein said at least one oxidizing agent is mixed with said dye composition at the time of use.

48. The process according to claim 46, wherein said at least one oxidizing agent is applied to said human keratin fibres in the form of an oxidizing composition simultaneously with or sequentially to the dye composition.

49. A process for the oxidation dyeing of human keratin fibres comprising applying to the human keratin fibres a dye composition comprising at least one monocationic monoazo dye of formula (I) below:

Formula (I)

wherein:

W$_1$ is chosen from 5-, 6-, 7- and 8-membered heterocycles of formula (II) below:

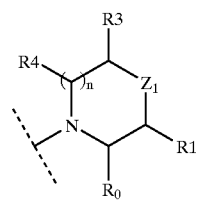

Formula (II)

W$_2$ is chosen from divalent, aromatic, and carbon-based pyridines and pyridazines of formula (III) below:

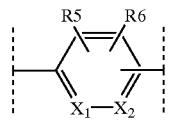

Formula (III)

W$_3$ is chosen from cationic heteroaromatic radicals of formula (IV) below:

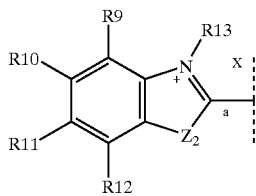

wherein in formulae (II), (III) and (IV):
n=0, 1, 2 or 3, provided that when n is greater than or equal to 2, then the $R_4$ radicals may be identical or different,
$X_1$ is chosen from a nitrogen atom and $CR_7$ radicals,
$X_2$ is chosen from a nitrogen atom and $CR_8$ radicals,
$Z_1$ is chosen from $CHR_2$ radicals, oxygen and sulphur atoms, and $NR_{14}$ radicals,
$Z_2$ is chosen from oxygen and sulphur atoms, and $NR_{15}$ radicals,
$R_0$, $R_1$, $R_2$, $R_3$, $R_4$, $R_5$, $R_6$, $R_7$, $R_8$, $R_9$, $R_{10}$, $R_{11}$ and $R_{12}$, which may be identical or different, are each chosen from a hydrogen atom, linear and branched $C_1$–$C_{10}$ hydrocarbon-based chains, possibly forming at least one carbon-based ring comprising from 3 to 6 members, and being saturated or unsaturated, wherein at least one carbon atom of the hydrocarbon-based chains may be replaced with an entity chosen from oxygen, nitrogen, and sulphur atoms, and an $SO_2$ group, and wherein the carbon atoms may be, independently of one another, substituted; $R_0$, $R_1$, $R_2$, $R_3$, $R_4$, $R_5$, $R_6$, $R_7$, $R_8$, $R_9$, $R_{11}$ and $R_{12}$ comprising no peroxide bond, nor any diazo or nitroso radicals,
$R_{14}$ is chosen from a hydrogen atom, linear and branched $C_1$–$C_{10}$ hydrocarbon-based chains, possibly forming at least one carbon-based ring comprising from 3 to 6 members, and being saturated or unsaturated, wherein at least one carbon atom of the hydrocarbon-based chains may be replaced with an entity chosen from oxygen, nitrogen, and sulphur atoms, and an $SO_2$ group, and wherein the carbon atoms may be, independently of one another, substituted, $R_{14}$ comprising no peroxide bond, nor any diazo or nitroso radicals; provided that said oxygen, nitrogen and sulphur atoms are not linked directly to the nitrogen atom carrying the $R_{14}$ radical,
$R_5$ with $R_6$ may optionally form a carbon-based aromatic ring,
$R_{13}$ and $R_{15}$, which may be identical or different, are each chosen from $C_1$–$C_8$ alkyl radicals optionally substituted with at least one radical chosen from hydroxyl, $C_1$–$C_2$ alkoxy, $C_2$–$C_4$ (poly)hydroxyalkoxy, unsubstituted and substituted amino, carboxyl, sulphonic, and phenyl radicals, which are optionally substituted;
the bond a of the cationic ring of formula (IV) is linked to the azo group of formula (I);
X is an anion chosen from organic and inorganic anions;
at least one oxidation base, and, optionally, at least one coupler, in the presence of at least one oxidizing agent.

50. The process according to claim 49, wherein said human keratin fibres are hair.

51. The process according to claim 49, wherein said at least one oxidizing agent is mixed with the dye composition at the time of use.

52. The process according to claim 49, wherein said at least one oxidizing agent is applied to the fibres in the form of an oxidizing composition simultaneously with or sequentially to the dye composition.

53. A multicompartment device or multicompartment dyeing kit for dyeing human keratin fibres, comprising a first compartment (1) comprising a composition comprising at least one monocationic monoazo dye of formula (I) below:

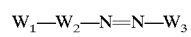

wherein:
$W_1$ is chosen from 5-, 6-, 7- and 8-membered heterocycles of formula (II) below:

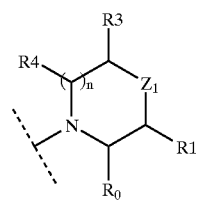

$W_2$ is chosen from divalent, aromatic, and carbon-based pyridines and pyridazines of formula (III) below:

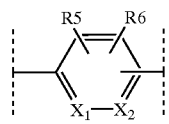

$W_3$ is chosen from cationic heteroaromatic radicals of formula (IV) below:

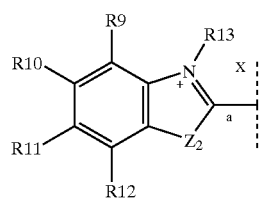

wherein in formulae (II), (III) and (IV):
n=0, 1, 2 or 3, provided that when n is greater than or equal to 2, then the $R_4$ radicals may be identical or different,
$X_1$ is chosen from a nitrogen atom and $CR_7$ radicals,
$X_2$ is chosen from a nitrogen atom and $CR_8$ radicals,
$Z_1$ is chosen from $CHR_2$ radicals, oxygen and sulphur atoms, and $NR_{14}$ radicals,
$Z_2$ is chosen from oxygen and sulphur atoms, and $NR_{15}$ radicals,
$R_0$, $R_1$, $R_2$, $R_3$, $R_4$, $R_5$, $R_6$, $R_7$, $R_8$, $R_9$, $R_{10}$, $R_{11}$ and $R_{12}$, which may be identical or different, are each chosen from a hydrogen atom, linear and branched $C_1$–$C_{10}$ hydrocarbon-based chains, possibly forming at least one carbon-based ring comprising from 3 to 6 members, and being saturated or unsaturated, wherein at least one carbon atom of the hydrocarbon-based chains may be replaced with an entity chosen from oxygen, nitrogen, and sulphur atoms, and an $SO_2$ group, and wherein the carbon atoms may be, independently of one another, substituted; $R_0$, $R_1$, $R_2$, $R_3$, $R_4$, $R_5$, $R_6$, $R_7$, $R_8$, $R_9$, $R_{11}$ and $R_{12}$ comprising no peroxide bond, nor any diazo or nitroso radicals, $R_{14}$ is chosen from a hydrogen atom, linear and branched $C_1$–$C_{10}$ hydrocarbon-based chains, possibly forming at least one carbon-based ring comprising from 3 to 6 members, and being saturated or unsaturated, wherein at least one carbon atom of the hydrocarbon-based chains may be replaced with an entity chosen from oxygen, nitrogen, and sulphur atoms, and an $SO_2$ group, and wherein the carbon atoms may be, independently of one another, substituted, $R_{14}$ comprising no peroxide bond, nor any diazo or nitroso radicals; provided that said oxygen, nitrogen and sulphur atoms are not linked directly to the nitrogen atom carrying the $R_{14}$ radical, $R_5$ with $R_6$ may optionally form a carbon-based aromatic ring, $R_{13}$ and $R_{15}$, which may be identical or different, are each chosen from $C_1$–$C_8$ alkyl radicals optionally substituted with at least one radical chosen from hydroxyl, $C_1$–$C_2$ alkoxy, $C_2$–$C_4$ (poly)hydroxyalkoxy, unsubstituted and substituted amino, carboxyl, sulphonic, and phenyl radicals, which are optionally substituted;

the bond a of the cationic ring of formula (IV) is linked to the azo group of formula (I);

X is an anion chosen from organic and inorganic anions, and a second compartment (2) comprising an oxidizing composition.

54. At least one monocationic monoazo dye of formula (I) below:

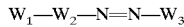

Formula (I)

wherein:

$W_1$ is chosen from 5-, 6-, 7- and 8-membered heterocycles of formula (II) below:

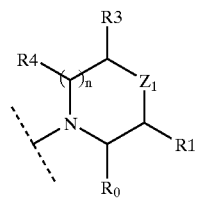

Formula (II)

$W_2$ is chosen from divalent, aromatic, and carbon-based pyridines and pyridazines of formula (III) below:

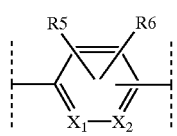

Formula (III)

$W_3$ is chosen from cationic heteroaromatic radicals of formula (IV) below:

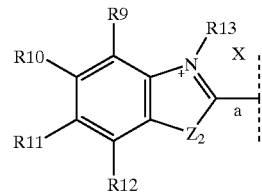

(IV)

wherein in formulae (II), (III) and (IV):

n=0, 2 or 3, provided that when n is greater than or equal to 2, then the $R_4$ radicals may be identical or different, $X_1$ is chosen from a nitrogen atom and $CR_7$ radicals, $X_2$ is chosen from a nitrogen atom and $CR_8$ radicals, $Z_1$ is chosen from $CHR_2$ radicals, oxygen and sulphur atoms, and $NR_{14}$ radicals, $Z_2$ is chosen from oxygen and sulphur atoms, and $NR_{15}$ radicals, $R_0$, $R_1$, $R_2$, $R_3$, $R_4$, $R_5$, $R_6$, $R_7$, $R_8$, $R_9$, $R_{10}$, $R_{11}$ and $R_{12}$, which may be identical or different, are each chosen from a hydrogen atom, linear and branched $C_1$–$C_{10}$ hydrocarbon-based chains, possibly forming at least one carbon-based ring comprising from 3 to 6 members, and being saturated or unsaturated, wherein at least one carbon atom of the hydrocarbon-based chains may be replaced with an entity chosen from oxygen, nitrogen, and sulphur atoms, and an $SO_2$ group, and wherein the carbon atoms may be, independently of one another, substituted; $R_0$, $R_1$, $R_2$, $R_3$, $R_4$, $R_5$, $R_6$, $R_7$, $R_8$, $R_9$, $R_{11}$ and $R_{12}$ comprising no peroxide bond, nor any diazo or nitroso radicals, $R_{14}$ is chosen from a hydrogen atom, linear and branched $C_1$–$C_{10}$ hydrocarbon-based chains, possibly forming at least one carbon-based ring comprising from 3 to 6 members, and being saturated or unsaturated, wherein at least one carbon atom of the hydrocarbon-based chains may be replaced with an entity chosen from oxygen, nitrogen, and sulphur atoms, and an $SO_2$ group, and wherein the carbon atoms may be, independently of one another, substituted, $R_{14}$ comprising no peroxide bond, nor any diazo or nitroso radicals; provided that said oxygen, nitrogen and sulphur atoms are not linked directly to the nitrogen atom carrying the $R_{14}$ radical, $R_5$ with $R_6$ may optionally form a carbon-based aromatic ring, $R_{13}$ and $R_{15}$, which may be identical or different, are each chosen from $C_1$–$C_8$ alkyl radicals optionally substituted with at least one radical chosen from hydroxyl, $C_1$–$C_2$ alkoxy, $C_2$–$C_4$ (poly)hydroxyalkoxy, unsubstituted and substituted amino, carboxyl, sulphonic, and phenyl radicals, which are optionally substituted;

the bond a of the cationic ring of formula (IV) is linked to the azo group of formula (I);

X is an anion chosen from organic and inorganic anions.

55. A method of preparing a direct dye composition for dyeing human keratin fibres comprising, including in said direct dye composition, at least one direct dye chosen from monocationic monoazo dyes of formula (I) below:

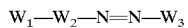

Formula (I)

wherein:

$W_1$ is chosen from 5-, 6-, 7- and 8-membered heterocycles of formula (II) below:

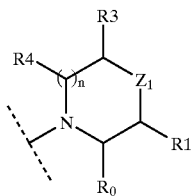

Formula (II)

$W_2$ is chosen from divalent, aromatic, an carbon-based pyridines and pyridazines of formula (III) below:

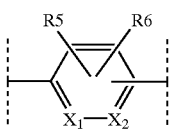

Formula (III)

$W_3$ is chosen from cationic heteroaromatic radicals of formula (IV) below:

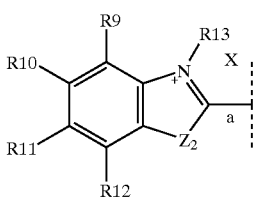

(IV)

wherein in formulae (II), (III) and (IV):
- n=0, 1, 2 or 3, provided that when n is greater than or equal to 2, then the $R_4$ radicals may be identical or different,
- $X_1$ is chosen from a nitrogen atom and $CR_7$ radicals,
- $X_2$ is chosen from a nitrogen atom and $CR_8$ radicals,
- $Z_1$ is chosen from $CHR_2$ radicals, oxygen and sulphur atoms, and $NR_{14}$ radicals,
- $Z_2$ is chosen from oxygen and sulphur atoms, and $NR_{15}$ radicals,
- $R_0$, $R_1$, $R_2$, $R_3$, $R_4$, $R_5$, $R_6$, $R_7$, $R_8$, $R_9$, $R_{10}$, $R_{11}$ and $R_{12}$, which may be identical or different, are each chosen from a hydrogen atom, linear and branched $C_1$–$C_{10}$ hydrocarbon-based chains, possibly forming at least one carbon-based ring comprising from 3 to 6 members, and being saturated or unsaturated, wherein at least one carbon atom of the hydrocarbon-based chains may be replaced with an entity chosen from oxygen, nitrogen, and sulphur atoms, and an $SO_2$ group, and wherein the carbon atoms may be, independently of one another, substituted; $R_0$, $R_1$, $R_2$, $R_3$, $R_4$, $R_5$, $R_6$, $R_7$, $R_8$, $R_9$, $R_{11}$ and $R_{12}$ comprising no peroxide bond, nor any diazo or nitroso radicals,
- $R_{14}$ is chosen from a hydrogen atom, linear and branched $C_1$–$C_{10}$ hydrocarbon-based chains, possibly forming at least one carbon-based ring comprising from 3 to 6 members, and being saturated or unsaturated, wherein at least one carbon atom of the hydrocarbon-based chains may be replaced with an entity chosen from oxygen, nitrogen, and sulphur atoms, and an $SO_2$ group, and wherein the carbon atoms may be, independently of one another, substituted, $R_{14}$ comprising no peroxide bond, nor any diazo or nitroso radicals; provided that said oxygen, nitrogen and sulphur atoms are not linked directly to the nitrogen atom carrying the $R_{14}$ radical,
- $R_5$ with $R_6$ may optionally form a carbon-based aromatic ring,
- $R_{13}$ and $R_{15}$, which may be identical or different, are each chosen from $C_1$–$C_8$ alkyl radicals optionally substituted with at least one radical chosen from hydroxyl, $C_1$–$C_2$ alkoxy, $C_2$–$C_4$ (poly)hydroxyalkoxy, unsubstituted and substituted amino, carboxyl, sulphonic, and phenyl radicals, which are optionally substituted;
- the bond a of the cationic ring of formula (IV) is linked to the azo group of formula (I);
- X is an anion chosen from organic and inorganic anions.

56. The method according to claim 55, wherein the human keratin fibres are hair.

* * * * *

UNITED STATES PATENT AND TRADEMARK OFFICE
CERTIFICATE OF CORRECTION

PATENT NO. : 6,824,570 B2
DATED : November 30, 2004
INVENTOR(S) : Vidal et al.

It is certified that error appears in the above-identified patent and that said Letters Patent is hereby corrected as shown below:

Column 19,
Line 63, "SO$_2$group," should read -- SO$_2$ group, --.

Column 21,
Lines 4 and 10, "according claim 1," should read -- according to claim 1, --.
Line 13, "according claim 10," should read -- according to claim 10, --.

Column 31,
Line 12, "an carbon-based" should read -- and carbon-based --.

Column 32,
Line 9, "SO$_2$group," should read -- SO$_2$ group, --.

Signed and Sealed this

Twenty-second Day of February, 2005

JON W. DUDAS
*Director of the United States Patent and Trademark Office*